United States Patent [19]
Werenicz

[11] Patent Number: 4,842,666
[45] Date of Patent: Jun. 27, 1989

[54] PROCESS FOR THE PERMANENT JOINING OF STRETCHABLE THREADLIKE OR SMALL RIBBONLIKE ELASTIC ELEMENTS TO A FLAT SUBSTRATE, AS WELL AS USE THEREOF FOR PRODUCING FRILLED SECTIONS OF FILM OR FOIL STRIP

[75] Inventor: Harald Werenicz, Luneburg, Fed. Rep. of Germany

[73] Assignee: H. B. Fuller Company, St. Paul, Minn.

[21] Appl. No.: 164,256

[22] Filed: Mar. 4, 1988

[30] Foreign Application Priority Data

Mar. 7, 1987 [DE] Fed. Rep. of Germany ....... 3707349
Nov. 28, 1987 [DE] Fed. Rep. of Germany ....... 3740410

[51] Int. Cl.$^4$ .................... B32B 31/10; B32B 31/12
[52] U.S. Cl. .................... 156/161; 156/291; 156/324; 427/208.6; 427/256; 428/198
[58] Field of Search ............. 156/160, 161, 164, 176, 156/178, 291, 324; 427/208.6, 256; 428/198

[56] References Cited

U.S. PATENT DOCUMENTS

| | | | |
|---|---|---|---|
| 4,081,301 | 3/1978 | Buell | 156/164 |
| 4,333,782 | 6/1982 | Pieniak | 156/164 |
| 4,543,141 | 9/1985 | Bradley et al. | 156/164 |
| 4,574,022 | 3/1986 | Johnson et al. | 156/164 |
| 4,711,683 | 12/1987 | Merkatoria | 156/164 |

FOREIGN PATENT DOCUMENTS

| | | |
|---|---|---|
| 0154068 | 3/1984 | European Pat. Off. . |
| 3347294C1 | 12/1983 | Fed. Rep. of Germany . |
| 3447449A1 | 12/1984 | Fed. Rep. of Germany . |
| 61-152801 | 7/1986 | Japan . |

*Primary Examiner*—Robert A. Dawson
*Attorney, Agent, or Firm*—Merchant, Gould, Smith, Edell, Welter & Schmidt

[57] ABSTRACT

The invention concerns a process for the permanent attachment or joining of threadlike or small ribbonlike elastic elements to a flat substrate by means of an adhesive that is characterized by the fact that one disposes, or fixes, in the desired position, one or several threadlike or small ribbonlike elastic elements on the flat substrate, or guides them in the desired position at a distance of about 1 to cm from the flat substrate, and covers these elastic elements, and some portion of the adjacent region of the substrate with a sprayed-on melt adhesive, and in the case of guiding at a distance, brings the threadlike or small ribbonlike elements into contact together with the fleece course. The invention further concersn application of the process for producing frilled section of foil course or film sheet with stretchable threadlike or small ribbonlike elements located in the respective edge region between a foil course or film and a covering layer, an absorbent layer disposed therebetween, and a covering section of fleece.

23 Claims, 7 Drawing Sheets

PROCESS FOR THE PERMANENT JOINING OF STRETCHABLE THREADLIKE OR SMALL RIBBONLIKE ELASTIC ELEMENTS TO A FLAT SUBSTRATE, AS WELL AS USE THEREOF FOR PRODUCING FRILLED SECTIONS OF FILM OR FOIL STRIP

FIELD OF THE INVENTION

The invention relates to a process for introducing into flat substrates elastic properties by the attachment of threadlike or ribbonlike elastic elements to the substrate through an adhesive composition. The adhesive composition can be a sprayed on melt adhesive that can be used in a variety of process steps to adhere the elastic element to the substrate.

BACKGROUND OF THE INVENTION

The invention concerns a process for the permanent joining of threadlike or small ribbonlike elements to a flat substrate by means of an adhesive, as well as the use of this process for producing frilled sections of a film sheet or a foil course (strip).

It is generally known, and in particular for the production of diaper pants or disposable diapers, e.g. from DE-OS No. 34 47 442 and DE-PS No. 33 47 294, that when joining threadlike or small ribbonlike elastic elements with a flat substrate either to provide the surfaces of two parts to be joined with an adhesive and to press these surfaces provided with adhesive together, or to provide only the threadlike or small ribbonlike elements, or only the flat substrate with the adhesive, whereafter both parts are pressed together. These types of processes, in particular in the case of producing bulk articles, are both time consuming and expensive for apparatus. For example, the adhesive must be applied with application rollers or nozzles to at least one of the elements to be glued together and this latter then pressed. Gluing threadlike elements to the flat substrate brings up problems, in particular in the case of the threadlike elements when dealing with an elastic thread held under tension, as is, for example, used for frilling tightly closing, flat structures made of plastic and/or irregular fiber fleece, as is required in the hygienic area, e.g. for a diaper or diaper pants, also in the case of work clothes, in order to enable a better fitting or snugging capability; similar problems arise when producing operating room caps and face masks used in the surgical field, and in the case of numerous other articles in the hygienic and medical area of application.

The invention provides a new process for the permanent joining of threadlike or small ribbonlike elastic elements to a flat substrate by means of an adhesive that is capable of being used without great expense, and that is suited for a permanent joining, in particular of threadlike elastic elements to a flat substrate and, actually, preferentially with an elastic thread under tension that is to be joined with a plastic film or foil underlay.

The invention also provides the use of this new joining process for elastic threads for producing desired sections of film sheet or foil course with stretchable threadlike or small ribbonlike elements located in the respective edge region between a film, or a foil and a covering layer, an absorbent inlay disposed therebetween, and with a section of fleece covering the absorbent inlay.

BRIEF DISCUSSION OF THE INVENTION

Hence, for meeting the objective in accordance with the invention, a process is disclosed of the initially mentioned kind that is characterized by the fact, prior to the application of the adhesive, that one or several threadlike or small ribbonlike elastic elements are disposed or fixed in the desired position, on or at a distance from the flat substrate, and that afterwards these threadlike or small ribbonlike elements as well as the adjoining area of the substrate are covered with a sprayable melt adhesive.

Surprisingly, it has been shown that one can glue threadlike or small ribbonlike elements to a flat substrate quite easily, without application of adhesive to the flat substrate or coating the threadlike or small ribbonlike element with adhesive, by covering or spraying with a sprayed on hot melt adhesive the threadlike or small ribbonlike element that is fixed and/or guided and disposed on, or at a slight distance away from the flat substrate, whereby the hot melt adhesive is also said to grasp the neighboring areas of the threadlike or small ribbonlike element, therefore the adjoining substrate areas.

In comparison to conventional adhesive processes, a gluing layer between the two items to be glued, namely the threadlike element and substrate, is not required. On the contrary, the formation of a finely divided spray of the melt adhesive that, when setting, deposits itself on the substrate in cobweb fashion as a fine web of extremely thin filaments of melt adhesive, about the threads and also in the neighborhood thereof, and holds the threadlike or small ribbonlike element firmly to the substrate. Depending upon pressure and temperature, and depending upon the type of melt adhesive, cobweblike sprayed filaments can be generated into patternlike, overlapping sprayed filaments and can be applied, for example, in a ringlike, oval or other more or less uniformly entwining arrangement.

Surprisingly, it has further been shown that a still better adhesion is achieved if one arranges the threadlike or small ribbonlike elements in the desired position at a distance from 0.1 to 3 cm from the flat substrate, and sprays these with a melt adhesive, whereby the threadlike or small ribbonlike element(s) are transported in the same direction with the substrate under the spray head and brought into contact by reducing the distance to the substrate.

The spray of the melt adhesive deposits itself not only as a fine web of extremely thin filaments of the melt adhesive about the thread(s), but rather hangs down therefrom, or lays down, partially, also over a neighboring thread and arrives, through the stream of air, under the thread(s) guided at some distance from the substrate course and therewith yields, upon contact between threads and substrate, a cobweblike, quasi 'spun-in' thread pattern on the substrate.

For the process in accordance with the invention, any known sprayable hot melt adhesives having a melting range from 80° to 200° C. and whose viscosity at these temperatures enables them to be sprayed at a pressure from 1 to 50 bar can be used. The hot melt adhesive in general has a softening point from 70° to 140° C. and a viscosity, at 150° C., within a range from about 500° to 40,000 mPa.s. The working range of these melt glues lies generally within a temperature range of 105° to 180° C.

DETAILED DISCUSSION OF THE INVENTION

Substrates include plastic films, sheets or foils of any kind, for example those of a polyethylene or polypropylene base, polyester, polyvinyl chloride, polyvinylidine chloride, etc., while used as threads to be attached to the substrate are usual type elastic rubber threads or plastic threads, but also elastic, small ribbonlike elements.

For example, for producing diaper pants that are to be frilled, gathered or pleated in the step region, plastic film is used as a substrate and as the covering layer is a course of fleece, between which the stretchable or stretched filamentlike or small ribbonlike element is fixed and/or glued. In general, the stretchable thread is glued by applying the cobweblike melt glue threads, most often by spraying of same, and pressed on immediately thereafter is the layer of fleece that joins itself in adhering fashion with the still adhesive melt glue. Analogously, the stretchable threads can first be joined with the fleece course that is then pressed with the film.

Although generating the cobweblike layer of melt glue is preferentially done by spraying on the stretchable threads that are fixed to the substrate, it is also possible to produce the melt glue web separately and to then cover threads and substrate.

In general, the threadlike or small ribbonlike elements can be fixed to the substrate in the stretched condition, e.g. mechanically or by self-tension. After gluing, this area pulls itself together and yields the desired frilling or gathering. In the area that is not to be frilled, no gluing occurs and the loose thread still under tensile stress on the substrate will be severed when cutting through the section of film.

In another form of embodiment of the process in accordance with the invention, it is possible to arrange the threads on the already pleated substrate in a non, or only slightly, stretched condition, and/or guide and glue them at some distance away. This process has the advantage that the stretchable threads not intended for the frilled area can be cut immediately behind the fold or frill. This process also can be carried out in continuous fashion, for example when producing diaper pants, by using a roller with appropriate depressions accommodating the areas to be frilled, in accordance with EU-Al No. 0 154 468.

According to another aspect of the present invention, the process in accordance with the invention can also be used for producing frilled sections of foil or film course or sheet with stretchable threadlike or small ribbonlike elements located in the respective edge area between a film and a covering layer, and with an absorbent inlay disposed therebetween and with a covering layer.

When producing diaper panties, it is not only that the frilled or the puckered section in the later stepping region of the diaper and covering with a layer of fleece is necessary; there still has to be provided an absorbent inlay lying in the center region of the film.. When producing these types of diapers, it is practical to glue the absorbent inlay in the striding area with the film or with an intermediate (intervening) layer laying on the film. Therefore, for simplifying the production process, used is the process in accordance with the invention.

In doing this, application of the cobweblike melt threads onto the stretchable thread is further extended to the intermediate area, between the respective, stretchable threads disposed at the edge of the course. Hence, one allows the spray fog from the melt adhesive not only to deposit on the stretchable threads in the associated regions and their adjacent area, rather also sprays the area lying between the stretchable threads, in order that the later-introduced course made of absorbent material adheres with the polyethylene film.

For optical and other reasons, it is in many cases practical to not spray this intermediate area directly on the polyethylene film, but rather to provide this thin layer of fleecy material in this center region with adhesive. This has the advantage that any gluing points that otherwise be on the polyethylene film inner surface and recognizable from the outside do not appear. With this application of cobweblike melt adhesive filaments in the intermediate area lying between the stretchable threads, the distribution of adhesive can be done such that the sprayed surface in the intermediate region is shorter than that in the edge regions.

BRIEF DISCUSSION OF DRAWINGS

The invention will be explained in more detail in the following with the aid of Drawings.

FIG. 1 shows a partially cut representation of a stretchable thread that is attached to a substrate based on the process in accordance with the invention, FIG. 2 shows a cut through a small stretchable ribbon attached to a substrate, with a covering layer of fleece material, FIG. 3 shows a cut representation analogous to FIG. 2, whereby, however, the small ribbon is now glued to a fleece as the substrate and covered over with a film as the covering layer, FIG. 4 shows two schematic representations of cobweblike and/or ornamentlike melt adhesive filaments, FIG. 5 shows a partially cut representation of the application of a non, or only slightly, stretched threadlike element on a prepleated course, FIG. 6 shows a schematic cut representation of the application of a slightly stretched thread with a continuous pleating wheel, FIG. 7 shows a schematic representation of the use of the process in accordance with the invention in the case of continuous production of diaper panties, FIG. 8 shows a partially cut representation of a stretchable thread, analogous to FIG. 1, that is guided (fed) at some distance from a substrate, sprayed and attached based on the process in accordance with the invention, FIG. 9 shows a schematic representation of how a stretched ribbon structure is sprayed at some distance from a substrate and guided therewith, and covered over with a covering layer.

Figure 8:
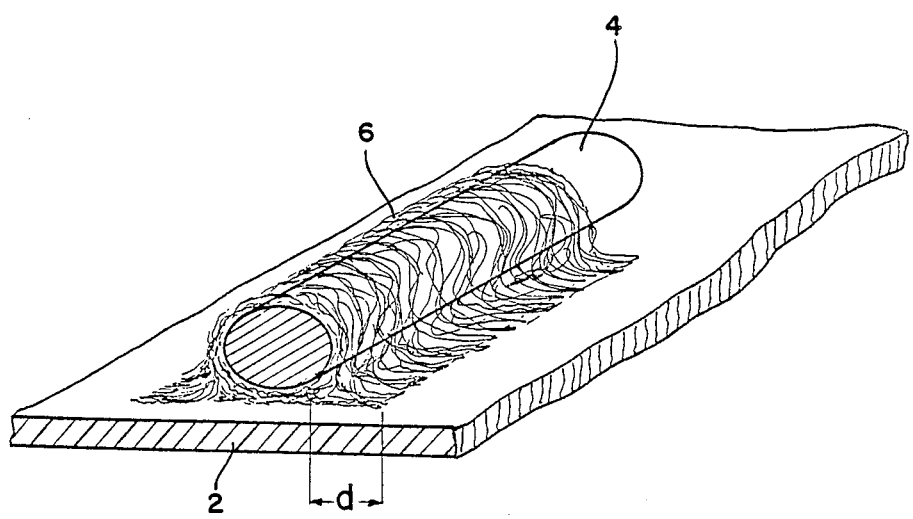

In the case of the form of embodiment shown in FIG. 8, where the thread has been guided (fed) at some distance from the substrate during spraying with adhesive and then brought into contact with the substrate, the cobweblike melt adhesive filaments are in part moved or pressed under the thread structure previously guided at a distance from the film; the rest cover the reachable surface of thread 4 and still lie on the adjoining area of the substrate 2.

Figure 1:
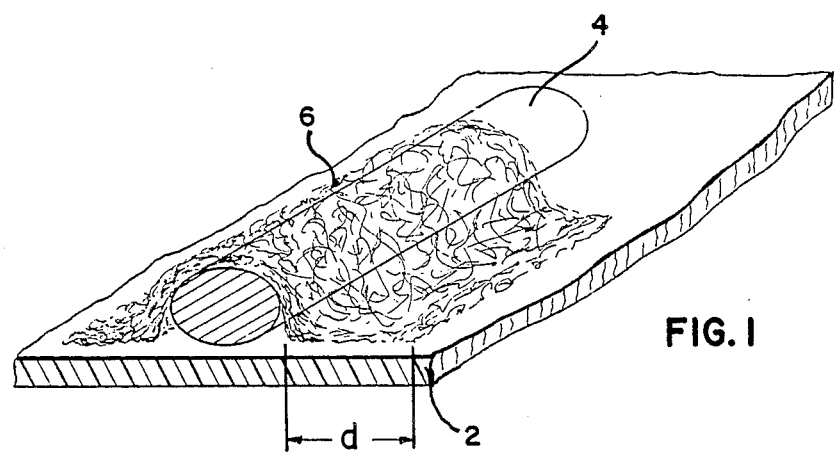
FIG. 1 and FIG. 8 show a section of a substrate 2 which, in the present case, is a polyethylene film or foil having a wall thickness of 50 μm. Placed thereupon is a thread 4 made of stretchable plastic and held with a plurality of cobweblike melt adhesive filaments lying one over the other.
Figure 2:
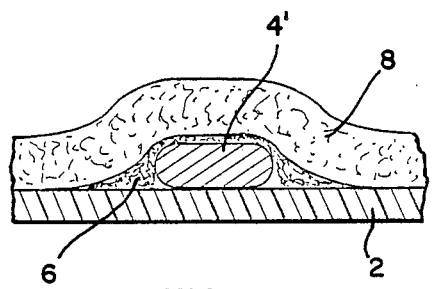
Figure 3:
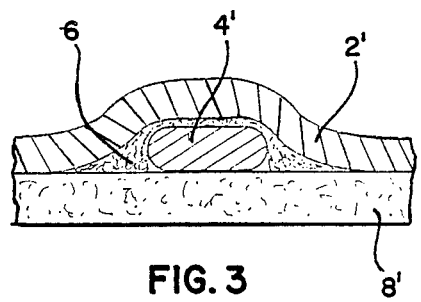
Figure 4:
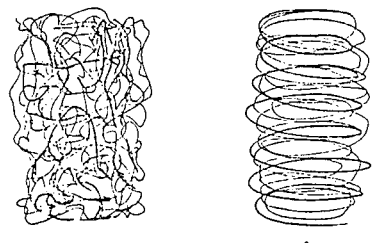

In the case of the forms of embodiment shown in FIG. 2 and FIG. 3, an elastic, small tape 4' on the substrate, which in FIG. 2 is polyethylene film or foil 2 and in FIG. 3 a polypropylene-tangled fleece 8', is glued with the cobweblike melt glue filament 6 to the substrate and to be covered with a covering layer, and actually with a polypropylene fleece 8 in accordance with FIG. 2, or with a polypropylene film 2' in FIG. 3.

Figure 5:
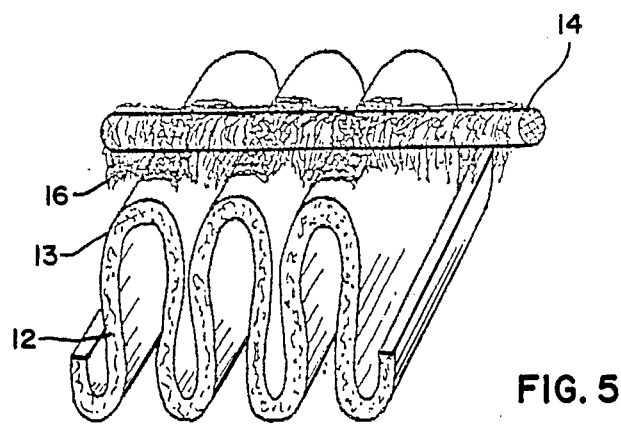

FIG. 5 shows how a prepleated substrate course 12 is covered over at its crest points 13, in this case by an only slightly, or not at all, stretched elastic ribbon 14, and covered with the melt glue filaments 16.

Figure 6:
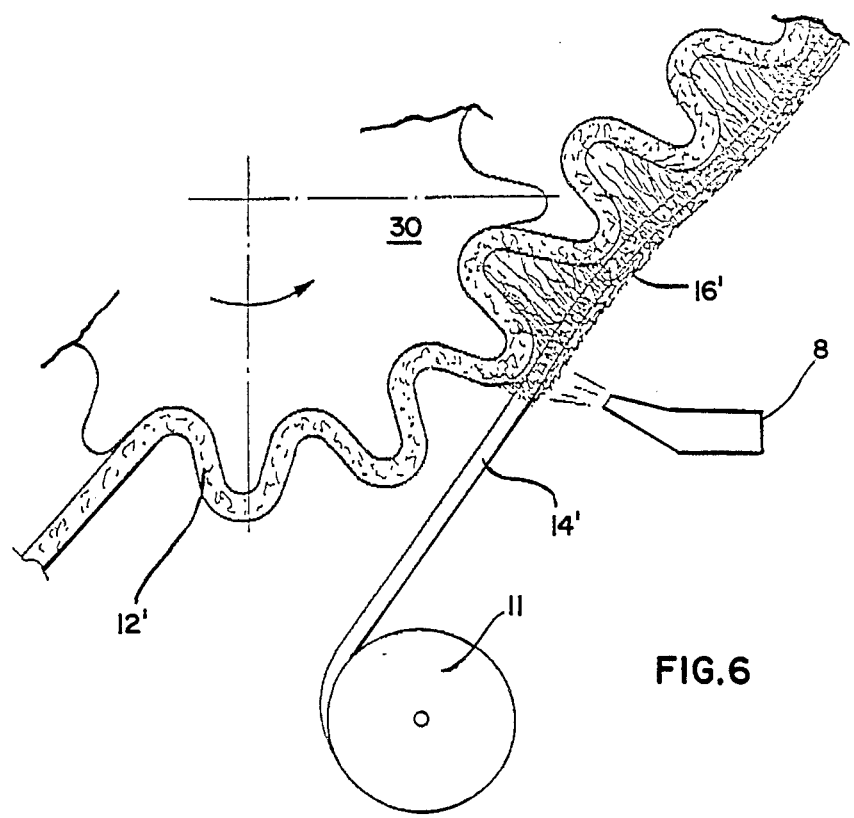

Analogously, in the case of the schematic representation shown in FIG. 6, the substrate 12' is brought into a pleated configuration by means of a frilling wheel or a frilling roller with depressions arranged at the periphery, whereby, in turn, placed tangentially on the crest points from a roll 11 is a stretchable thread 14' and glued with plastic filaments 16' by means of nozzles, and drawn in the running direction for further processing.

Figure 7:
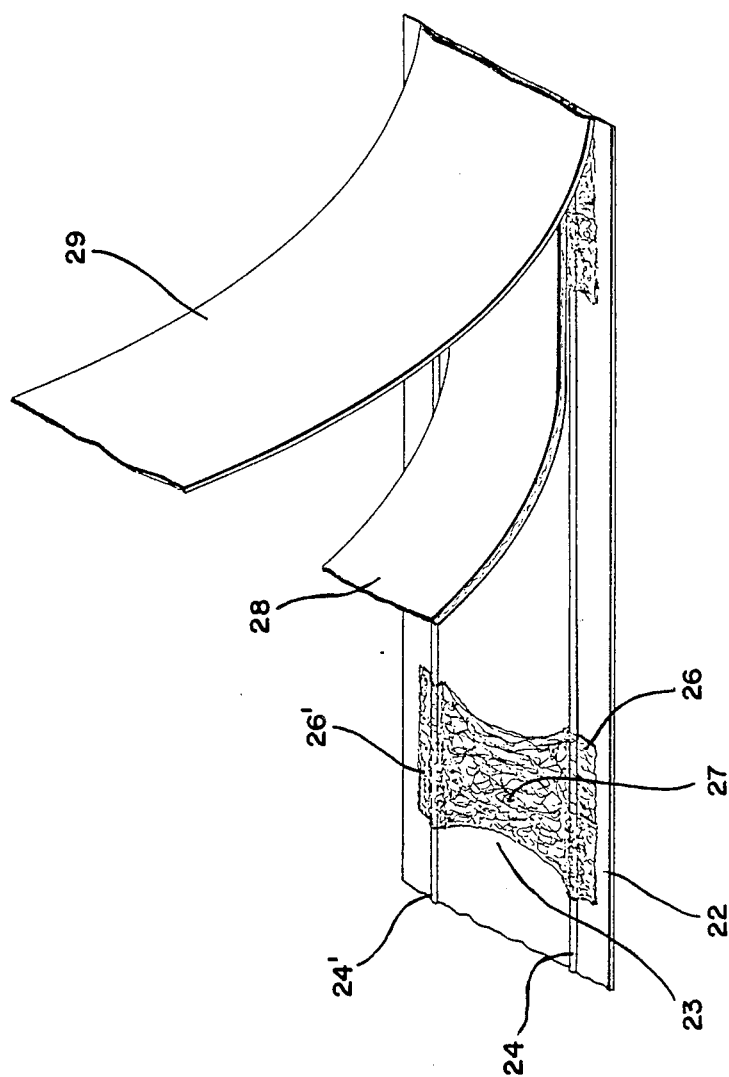

In the case of use of the process in accordance with the invention represented schematically in FIG. 7 for producing a film suitable for diaper panties, the film 22, as the substrate, is guided (fed) to a first station at which two elastic or stretchable threads 24, respectively 24' are disposed in the edge region and sprayed with melt adhesive in the areas 26 and 26'. The adhesive as usual at a distance from 1 to 15 mm from the side edge of the thread, is joined with the substrate by sprayed on melt adhesive filaments, however in the present case spraying is also done in the center region 27 of the substrate, whereby the limiting lines of the sprayed region 27 lying transversely to the direction of the course are drawn in concavely toward the center of the axis, as is shown at 23.

Installed at a second station is an absorbent inlay 28, as a course in the center region between the elastic threads 24, 24', this is then covered at a third station with a fleece course 29, up to over the area of the stretchable threads 24 and 24' that are covered with melt adhesive, and finally pressed together. At the end of this station, the individual film sections are cut into sections 31 with a cutting tool.

Figure 9:
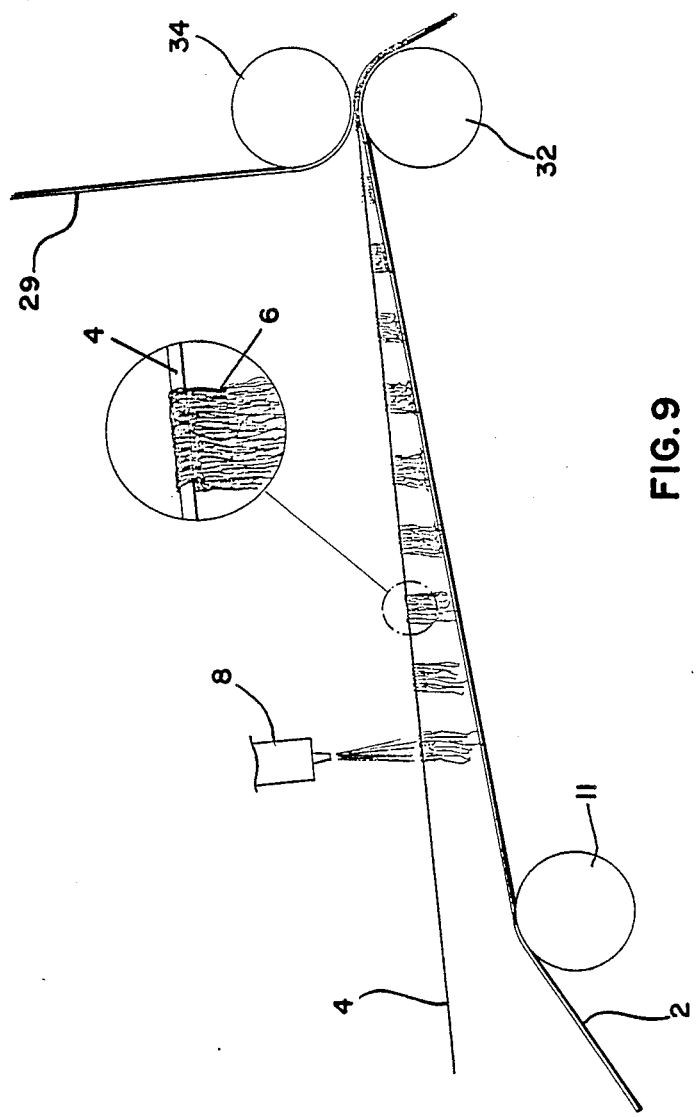
Figure 10:
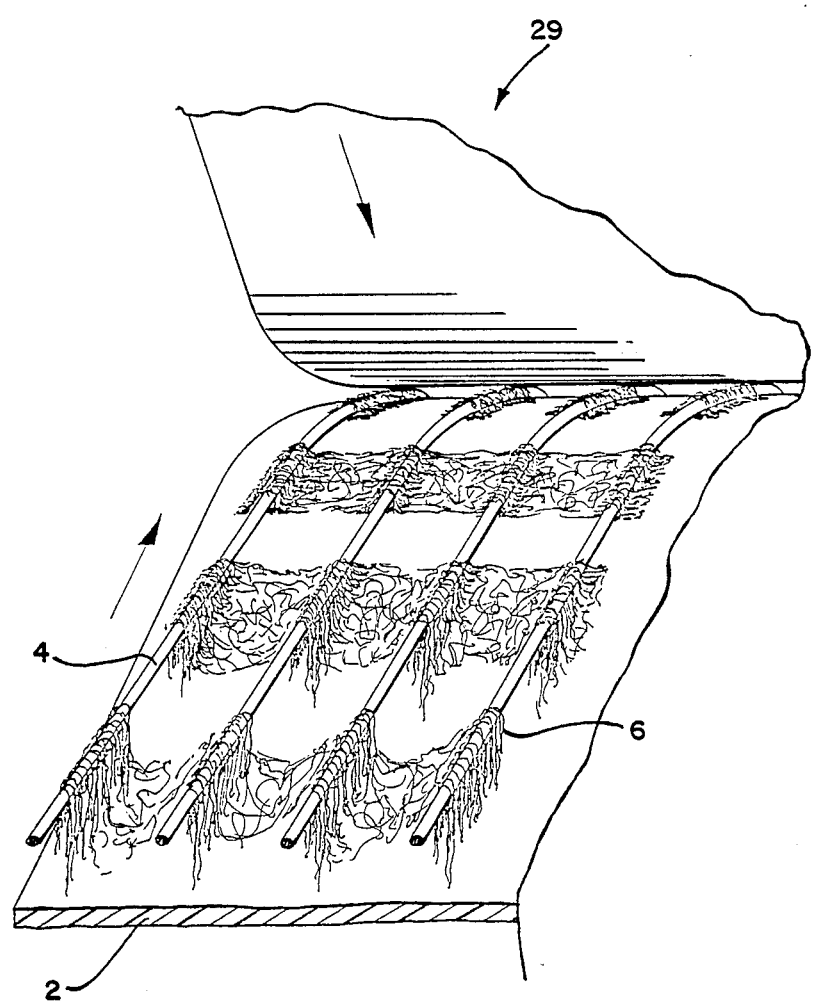
FIG. 10 shows a view analogous to FIG. 2.

In the case of the initially-mentioned variant of the process, with guiding of the elastic ribbons 4 at some distance relative to the substrate 2, as shown in FIG. 9 and FIG. 10, the elastic, small ribbons 4 are guided at some distance to the substrate, which for example is a polyethylene film 2, whereby the melt glue threads 6 sprayed on via a nozzle 8 hang down and, guided together with the substrate course, distribute themselves with reduction of the distance e.g. initially about 1 to 2 cm, until coming into contact with the film 2 and also arrive under the thread structure, and finally are adhered with the cobweblike melt glue filaments 6 to the substrate 2 and are covered with a covering layer, and actually with a polypropylene fleece 29. The film 2 is fed to the glue spray station via a roll 11 and is led off over the roller 32. Located above this roller 32 is a roller 34 feeding a fleece course 29. Contact of the small ribbon 4 covered with adhesive threads 6 with the substrate 2 occurs in the gap between the rollers 32 and 34, or shortly ahead of this, whereby the downwardly hanging adhesive film 6 has already come into contact with the substrate 2 that is guided at an acute angle of about 5° to 10° to the small ribbon 4, and form a cobweblike 'bed' or an underlay of adhesive filaments for the small ribbon 4. Also occurring in the gap region of rollers 32 and 34 is joining of the guided fleece course 29 with the substrate 2, whereby adhesion of these follows by means of the melt adhesive sprayed on over the width (d) to both sides of the small ribbon 4. In similar manner, it is also possible, before or instead of the fleece course, to apply an absorbent inlay 28, as is shown in FIG. 7, whereafter, if necessary, the fleece course is guided, at another station, to the substrate and joined therewith.

Figure 11:
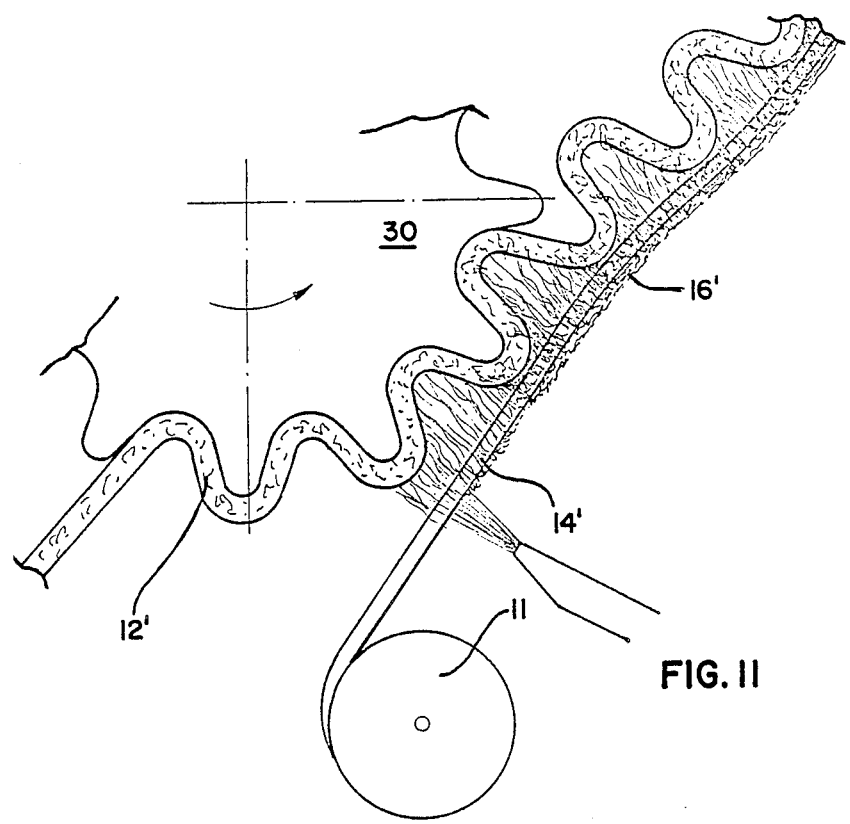
FIG. 11 shows a schematic cut representation of application of a slightly stretched thread, analogous to FIG. 6, with a continuous pleating wheel.

In the case of the variant of the process with guiding of the small ribbon 4 at a slight distance relative to the substrate 2 and unwinding of a non, or only slightly, stretched elastic small ribbon 4 onto an already prepleated substrate 12, respectively 12' to be attached analogously to FIG. 5 or to FIG. 6, as is shown in FIG. 11, spraying of the melt glue in the running direction of the substrate course 12' and of the elastic small ribbon 14' is somewhat shortened, hence in the direction toward the feed roller 11 that feeds (guides) the small elastic ribbon or ribbons 14' to the substrate 12' that is transported in the pleating wheel 30. In the case of this variant of the process, the adhesive is sprayed onto the small elastic ribbon 14' before it comes into contact with the pleated substrate at its crest points. Here, formed underneath the small elastic ribbon, analogously to FIG. 8 to 10, is a 'bed' made up of a web of glue filaments upon which the elastic small ribbon lies, and is further adhered in cobweblike fashion from above through the web of glue filament respectively with the substrate.

The invention will be explained in more detail in the following with the aid of Examples.

EXAMPLE 1

In the case of a hygienic article, in order to bring a substrate made of a polyethylene film having a thickness of 20–25 $\mu$m into a frilled condition, fixed onto this film was a stretched elastic thread made of polyether copolymer (e.g. LYCRA ® XA) with a thread caliber of 940 dtex, and after fixing, sprayed intermittently in sections of 25 cm in length, with a melt glue consisting of 50% hydrocarbon resin with a R+K softening point of 115° C., 30% of a styrene-butadiene-styrene-block copolymer and 20% mineral oil at a temperature of 175° C. at pressures from 2 to 8 bar, over a width region of 15 mm, with the application density mounting to 2 g/m$^2$. Next, the film with the glued threads was cut transversely in the unsprayed areas, whereby the desired frilled sections of course were obtained.

EXAMPLE 2

In another experiment, we proceeded in analogous fashion to Example 1, whereby finally a polypropylene spun fleece having a thickness of about 0.22 mm and an area weight of approximately 20 g/m$^2$ was pressed onto the threads attached beforehand, so that the entire region of the film was covered over with this spun fleece at a given distance from the edge of the film, said spun fleece adhering to the threadlike ribbon that was covered with melt glue.

EXAMPLE 3

A stretchable ribbon of polyether copolymer having a width of 3 mm and a thickness of 0.3 mm was fixed to a thermally joined polypropylene piled fiber fleece and sprayed with the melt glue in accordance with Example 1 over a width area of 10 mm, with the density of deposit amounting to 42 g/m². Next, pressed on was a polypropylene film and the construct obtained was processed further in sections.

EXAMPLE 4

Analogously to FIG. 6, supplied to a continuously operating system for producing diaper panties was a polyethylene film having a width of 22 cm that was provided with approximately 7 mm deep pleats, at an interval of 3 mm, sectionally, with the frilling roller shown in FIG. 6. Carried along in the direction of the course, under slight tension, in the edge region of the film, were one each stretchable ribbon made of polyurethane that was intermittently sprayed with adhesive and then pulled from the frilling roller and processed further.

EXAMPLE 5

As was shown in FIG. 7, a smooth film made of polyethylene was processed on a diaper system; fixed under tensile stress onto the film course were two stretchable bands made of a polyurethane thread, analogously to Example 1, and sprayed with the melt adhesive in accordance with Example 1. The cobweblike melt glue depositing itself had in each case a distance of 10 mm outwardly from the stretchable bands, however also extended into the center region 27 between the two bands, with deposit of the melt glue being carried out with three spray heads, the two outer of which for deposit onto the stretchable bands were correspondingly narrow and long, and that for the center region wider and shorter. Immediately thereafter, introduced into the region between the bands was an absorbent fiber course having a thickness of about 12 mm, and finally covered over with the polypropylene spun fleece course 29 used in Example 3. At the end of the station, the completed course was cut through into individual sections with a cutting tool, transversely to the course direction.

EXAMPLE 6

In a variant of the process according to Example 5, laid in with the film being supplied, in the region between the stressed threads, was a thin course of polypropylene piled fiber, whereby, with the later application of the adhesive to the threads and to the center region, the melt adhesive did not come into contact with the polyethylene film in the center region 27, and glued along with it only the absorbent inlay in the striding region. Since this intermediately laid layer of fleece was fixed to the polyethylene film beforehand, the absorbent inlay in the frilled area can not sideslip, particularly since it is afterwards still covered over with the covering layer that is likewise glued with the plastic film at the edge regions.

EXAMPLE 7

In the case of a hygienic article, in order to bring a substrate made of a polyethylene film having a thickness of 20 to 25 μm into a frilled condition, analogously to Example 1, the stretched elastic threads made of a polyethylene copolymer (e.g. LYCRA® XA) having a thread caliber of 940 dtex, were now guided (fed) at a distance of 10 mm from thid film, and intermittently sprayed with a melt glue analogously to Example 1, with the film being finally guided into contact with the thread structure and being cut off transversely in the unsprayed regions, whereafter obtained were the desired, frilled sections of course.

EXAMPLE 8

In the case of another experiment, work was carried out analogously to Example 7, whereby corresponding to Example 2, a polyproplene spun fleece having a thickness of about 0.22 mm and an area weight of about 20 g/m² was pressed on, after contact and/or gluing of the elastic small ribbons with substrate, so that the entire region of the film, at a given distance from the edge of the film, was covered over with this spun fleece, which adhered to the threadlike ribbon that was covered with the melt glue.

EXAMPLE 9

Analogously to Example 3, a stretchable ribbon made of polyether copolymer having a width of 3 mm and a thickness of 0.3 mm, was supplied to a thermically joined polypropylene piled fiber fleece and sprayed over an area width of 10 mm with the melt glue in accordance with Example 7, with the deposit density amounting to 42 g/m²; gluing follows after decreasing the distance, whereafter pressed on is a polyethylene film and the course obtained was further processed in sections.

EXAMPLE 10

Analogously to FIG. 11, supplied to a continously operating system for producing diaper panties was a polypropylene film having a width of 22 cm that was provided with the frilling roller, sectionwise by vaccum, with approximately 7 mm deep pleats, at an interval of 3 mm. Carried along in the course direction, under slight tension, respectively in the edge region of the film, was a stretchable ribbon made of polyurethan e that was sprayed intermittently with adhesive, whereby application of the melt glue threads followed at about 20 to 30 pleats apart in the direction of the course, at the contact points between film and the stretchable ribbon. Finally, the pleated course with glued-on ribbon was withdrawn from the frilling roller and processed further.

EXAMPLE 11

As was shown in FIG. 7, a smooth film made of polyethylene was processed on a diaper system; at some distance from the film, guided were two stretchable strips made of polyurethane band analogously to Example 7, under tensile stress, at some distance from the film, and sprayed with the melt adhesive in accordance with Example 7. The weblike melt glue depositing itself in each case had an interval of 10 mm outwardly from the stretchable bands, however also extended into the center region 27 between the two bands, with deposit of the melt glue being carried out with three spray heads, the two outer of which for deposit onto the stretchable bands being correspondingly narrow and long, and that for the center region wider and shorter. After contact of substrate and stretchable polyurethane bands, introduced into the area between the bands was an absorbent fiber course having a thickness of about 12 mm, and this latter was finally covered over with the polypropylene spun fiber fleece course 29 used in Example 9. At the end of the station, the completed course was cut through transversely to the direction of the course into individual sections with a cutting tool.

EXAMPLE 12

In a variant of the process according to Example 11, laid in with the film being supplied, in the region between the stressed bands or ribbons, was a thin course of thick absorbent cellulosic inlay, mat or ply, whereby, with the later application of the adhesive to the threads and to the center region, the melt adhesive did not come into contact with the polypropylene film in the center region 27, and only glued along with it the absorbent inlay in the striding region. Since this intermediately laid layer was fixed to the polyethylene beforehand, the absorbent inlay in the frilled area cannot sideslip (creep), particularly since it is afterwards still covered over with the covering layer that is likewise glued with the plastic film at the edge regions.

Achieved in all cases is an excellent durability of gluing, in particular against so-called 'creeping'; moreover, with the process in accordance with the invention, it is possible to obtain a thread structure, with a lesser prestressing of only 100% —as compared to 300% in the case of usual type processes—which leads to a much more flexible fitting of diapers, for example. Further the use of intermittent attachment of the elastic to the film substrate allows better contraction of the gathered region than the continuously attached elastic to a continuous glue line.

I claim:

1. A process for the permanent joining of stretchable threadlike or small ribbonlike elements to a flat substrate by means of an adhesive, characterized by the fact that, prior to application of the adhesive, one or several threadlike or small ribbonlike elastic elements (4) are disposed or fixed in the desired position at some distance from, the flat substrate (2), and that afterwards these threadlike or small ribbonlike elements (4) as well as the adjoining area of the substrate (2) are covered with a sprayable melt adhesive (6).

2. A process according to claim 1, characterized by the fact that the melt adhesive is sprayed on in the form of cobweblike to patternlike overlapping, small sprayed threads having a diameter from 20 to 400 mm.

3. A process according to claim 2, characterized by the fact that the threadlike or small ribbonlike element(s) and the adjoining areas are sprayed with the adhesive and covered over a width (d) from 1 to 15 mm, measured from the longitudinal edge of the threadlike or small ribbonlike element.

4. A process according to claim 2, characterized by the fact that the threadlike or small ribbonlike element(s) (4) disposed at some distance from the substrate, and areas of the substrate lying thereunder, are sprayed or covered with the adhesive over a width (d) from 1 to 15 mm, measured from the longitudinal edge of the threadlike or small ribbonlike element joined thereafter with the substrate and/or the element(s) located at the edge.

5. A process according to claim 4, characterized by the fact that the melt adhesive is applied in an amount from 2 to 100 g/m² to the threadlike or small ribbonlike element(s) (4).

6. A process according to claim 5, characterized by the fact that the melt adhesive is applied in an amount from 5 to 40 g/m² to the threadlike or small ribbonlike element.

7. A process according to claim 6, characterized by the fact that the melt adhesive is sprayed on continuously or intermittently.

8. A process according to claim 7, characterized by the fact that the threadlike or small ribbonlike element consisting of natural or synthetic rubber or plastic is fixed on the substrate under tension.

9. A process according to claim 1, characterized by the fact that one or several threadlike or small ribbonlike elements (4) that are disposed in the desired position at some distance from the flat substrate (2) and that have been sprayed with the melt adhesive (6), are transported in the same direction with the substrate under the spraying head and are brought into contact by reducing the distance to the substrate.

10. A process according to claim 9, characterized by the fact that the threadlike or small ribbonlike elements consist of a stretchable material and are continuously maintained under tensile stress during spraying and when in contact with the substrate.

11. A process according to claim 10, characterized by the fact that the threadlike or small ribbonlike elements (4) under stress that have been sprayed with the melt adhesive at a distance from 0.5 to 3 cm from the substrate are joined together with the substrate at an acute angle.

12. A process according to claim 11, characterized by the fact that the threadlike or small ribbonlike elements under stress are sprayed with melt adhesive outside the substrate course and then joined with the substrate course.

13. A process according to claim 1, characterized by the fact that there is disposed, at least on the projecting areas (13) of a frilled or pleated substrate (12), a threadlike or small ribbonlike element (14) that is not, or only slightly, under stress, and afterwards is sprayed with the melt adhesive (16).

14. A process according to claim 11, characterized by the fact that disposed or guided at some distance away, at least on the projecting areas (13) of a frilled or pleated substrate (12), is one or several threadlike or small ribbonlike elements (14) that are not, or only slightly, under stress, and afterwards are sprayed with the melt adhesive (16) before they are brought into contact with the substrate.

15. A process according to claim 14, characterized by the fact that used as a substrate (2) is a plastic film, an impregnated paper or a fleece.

16. A process according to claim 1, characterized by the fact that placed onto the substrate and the threadlike or small ribbonlike element immediately after spraying on the melt adhesive is a covering layer, and this latter is pressed on if necessary.

17. A process according to claim 9, characterized by the fact that there is placed onto the substrate and onto the threadlike or small ribbonlike element(s), after spraying on the melt adhesive, and immediately after bringing these latter together with the substrate, a covering layer and this latter is pressed on if necessary.

18. A process according to claim 16, characterized by the fact that used as a substrate is a fleece (8') and as a covering layer a film (2').

19. A process according to claim 17, characterized by the fact that used as a substrate is a fleece (8') and as a covering layer a film (2').

20. A process according to claim 1, characterized by the fact that the threadlike or small ribbonlike elements disposed or supplied in the edge area (26, 26') of a substrate present as a film (22) are sprayed with melt adhesive in the direction of the course, over a like length, or longer, area than the film area (27) lying between the elements.

21. A process according to claim 1 for producing frilled sections of film, with stretchable threadlike or small ribbonlike elements located in the respective edge area between a film and a covering layer, an absorbent inlay disposed therebetween, and a layer of felt covering these latter, further characterized by the additional steps of:
 (a) placing or fixing on the film (22) serving as a substrate, in the respective, later-frilled edge areas, either on this film
  (i) in the frilled or pleated condition one or several not, or slightly, stretched,
  (ii) in the flatly laid condition, one or several threadlike or small ribbonlike elements (24, 24'),
 (b) intermittently spraying with the melt adhesive the respective threadlike or small ribbonlike elements, as well as their adjoining areas, and simultaneously the area (27) lying between the threadlike or small ribbonlike elements,
 (c) next, placing on the area (27) sprayed with melt adhesive between the threadlike or small ribbonlike elements a course made of an absorbent padding material (28),
 (d) placing onto the film (22) and the course made of absorbent padding material (28) a fleece course (29), in a manner such that this latter covers the absorbent padding material (28) and also lies over the threadlike or small ribbonlike elements (24, 24') sprayed with the melt adhesive,
 (e) pressing the fleece course (29), at least in the area of the threadlike or small ribbonlike elements, together with these latter and,
 (f) cutting off the thusly obtained bonded material in sections transversely to the course direction.

22. A process according to claim 9 for producing frilled sections of film, with stretchable threadlike or small ribbonlike elements located in the respective edge area between a film and a covering layer, an absorbent inlay disposed therebetween, and a layer of fleece covering these latter, further characterized by the steps of:
 (a) holding or guiding one or several threadlike or small ribbonlike elements under tensile stress at some distance from the film serving as a substrate, at least in the respective, later-frilled edge areas of this film,
 (b) spraying with melt adhesive the respective threadlike or small ribbonlike elements, as well as their adjoining areas, and simultaneously the area lying between the threadlike or small ribbonlike elements,
 (c) next, bringing the threadlike or small ribbonlike elements sprayed with the melt adhesive into contact with the substrate by guiding them together,
 (d) afterwards, placing on the area between the threadlike or small ribbonlike elements sprayed with melt adhesive a course made of absorbent padding material,
 (e) placing onto the film and the course made of absorbent padding material a fleece course, in such a manner that this latter covers the absorbent padding material and also lies over the area of the threadlike or small ribbonlike elements sprayed with melt adhesive,
 (f) pressing the fleece course, at least in the area of the threadlike or small ribbonlike elements, together with these latter and,
 (g) cutting the thusly obtained bonded material into sections transversely to the direction of the course.

23. A process according to claim 22, characterized by the fact that the areas of the threadlike or small ribbonlike elements guided at a distance of 3 to 0.5 cm from the film, and sprayed with melt adhesive, are guided together with the film at an acute angle and, finally, applied is the course made of absorbent padding material and the fleece course.

* * * * *

UNITED STATES PATENT AND TRADEMARK OFFICE
CERTIFICATE OF CORRECTION

PATENT NO. : 4,842,666

DATED : June 27, 1989

INVENTOR(S) : Harald Werenicz

It is certified that error appears in the above-identified patent and that said Letters Patent is hereby corrected as shown below:

In Column 9, line 42, "mm" should read -- $\mu$m --.

Signed and Sealed this

Fifth Day of May, 1992

Attest:

DOUGLAS B. COMER

Attesting Officer

Acting Commissioner of Patents and Trademarks

REEXAMINATION CERTIFICATE (1807th)
United States Patent [19]
Werenicz

[11] B1 4,842,666

[45] Certificate Issued  Oct. 13, 1992

[54] PROCESS FOR THE PERMANENT JOINING OF STRETCHABLE THREADLIKE OR SMALL RIBBONLIKE ELASTIC ELEMENTS TO A FLAT SUBSTRATE, AS WELL AS USE THEREOF FOR PRODUCING FRILLED SECTIONS OF FILM OR FOIL STRIP

[75] Inventor: Harald Werenicz, Luneburg, Fed. Rep. of Germany

[73] Assignee: H. B. Fuller Company, St. Paul, Minn.

Reexamination Request:
No. 90/002,348, May 16, 1991

Reexamination Certificate for:
Patent No.: 4,842,666
Issued: Jun. 24, 1989
Appl. No.: 164,256
Filed: Mar. 4, 1988

Certificate of Correction issued May 5, 1992.

[30] Foreign Application Priority Data

Mar. 7, 1987 [DE] Fed. Rep. of Germany ....... 3707349
Nov. 28, 1987 [DE] Fed. Rep. of Germany ....... 3740410

[51] Int. Cl.$^5$ .................... B32B 31/10; B32B 31/12
[52] U.S. Cl. .................... 156/161; 156/291; 156/324; 427/208.6; 427/256; 428/198

[58] Field of Search ............ 156/160, 161, 164, 176, 156/178, 291, 324; 427/208.6, 256; 428/196; 604/385.2

[56] References Cited

U.S. PATENT DOCUMENTS
4,626,305  12/1986  Suzuki et al. .................... 156/229 X

FOREIGN PATENT DOCUMENTS
61-152801  7/1986  Japan .

*Primary Examiner*—Jeff H. Aftergut

[57] ABSTRACT

The invention concerns a process for the permanent attachment or joining of threadlike or small ribbonlike elastic elements to a flat substrate by means of an adhesive that is characterized by the fact that one disposes, or fixes, in the desired position, one or several threadlike or small ribbonlike elastic elements on the flat substrate, or guides them in the desired position at a distance of about 1 to cm from the flat substrate, and covers these elastic elements, and some portion of the adjacent region of the substrate with a sprayed-on melt adhesive, and in the case of guiding at a distance, brings the threadlike or small ribbonlike elements into contact together with the fleece course. The invention further concerns application of the process for producing frilled section of foil course or film sheet with stretchable threadlike or small ribbonlike elements located in the respective edge region between a foil course or film and a covering layer, an absorbent layer disposed therebetween, and a covering section of fleece.

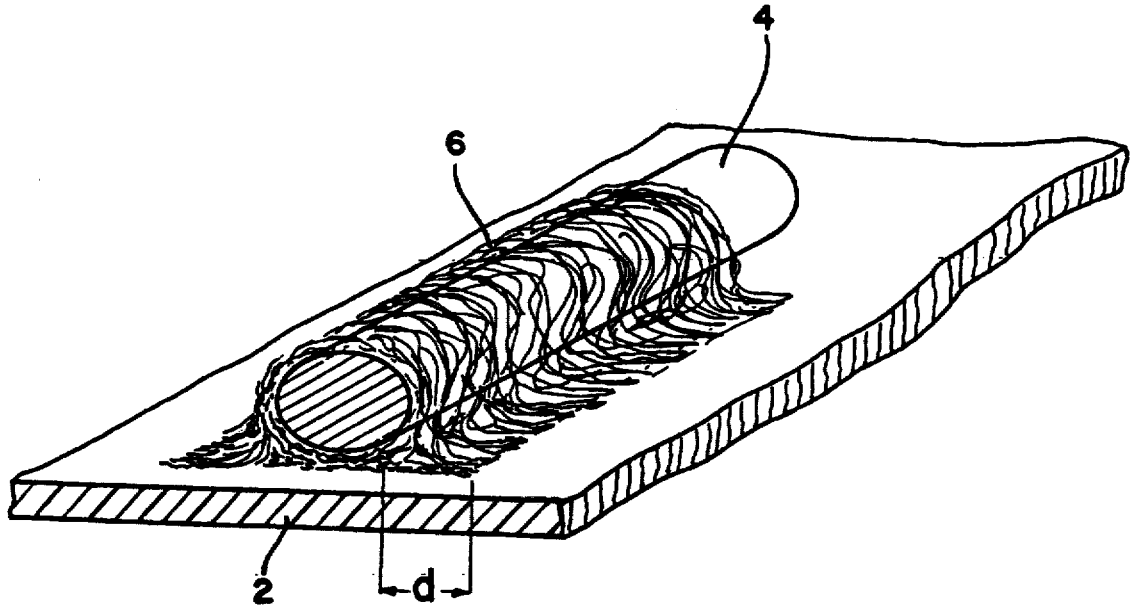

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Matter enclosed in heavy brackets [ ] appeared in the patent, but has been deleted and is no longer a part of the patent; matter printed in italics indicates additions made to the patent.

The patentability of claims 13, 20 and 21 is confirmed.

Claim 1 is cancelled.

Claims 2, 9, 16 and 22 are determined to be patentable as amended.

Claims 3–8, 10–12, 14, 15, 17–19, and 23 dependent on an amended claim, are determined to be patentable.

2. A process according to claim 1, characterized by the fact that the melt adhesive is sprayed on in the form of cobweblike to patternlike overlapping, small sprayed threads having a diameter from 20 to 400 [mm] *μm*.

9. A process according to claim [1] *2*, characterized by the fact that one or several threadlike or small ribbonlike elements (4) that are disposed in the desired position at some distance from the flat substrate (2) and that have been sprayed with the melt adhesive (6), are transported in the same direction with the substrate under the spraying head and are brought into contact by reducing the distance to the substrate.

16. A process according to claim [1] *2*, characterized by the fact that placed onto the substrate and the threadlike or small ribbonlike element immediately after spraying on the melt adhesive is a covering layer, and this latter is pressed on if necessary.

22. A process according to claim [9] *2*, for producing frilled sections of film, with stretchable threadlike or small ribbonlike elements located in the respective edge area between a film and a covering layer, an absorbent inlay disposed therebetween, and a layer of fleece covering these latter, further characterized by the steps of:

(a) holding or guiding one or several threadlike or small ribbonlike elements under tensile stress at some distance from the film serving as a substrate, at least in the respective, later-frilled edge areas of this film, (b) spraying with melt adhesive the respective threadlike or small ribbonlike elements, as well as their adjoining areas, and simultaneously the area lying between the threadlike or small ribbonlike elements, (c) next, bringing the threadlike or small ribbonlike elements sprayed with the melt adhesive into contact with the substrate by guiding them together, (d) afterwards, placing on the area between the threadlike or small ribbonlike elements sprayed with melt adhesive a course made of absorbent padding material, (e) placing onto the film and the course made of absorbent padding material a fleece course, in such a manner that this latter covers the absorbent padding material and also lies over the area of the threadlike or small ribbonlike elements sprayed with melt adhesive, (f) pressing the fleece course, at least in the area of the threadlike or small ribbonlike elements, together with these latter and, (g) cutting the thusly obtained bonded material into sections transversely to the direction of the course.

* * * * *